United States Patent [19]

Giles et al.

[11] Patent Number: 5,336,781
[45] Date of Patent: Aug. 9, 1994

[54] PROCESS

[75] Inventors: Robert Giles; Timothy C. Walsgrove, both of Tonbridge, England

[73] Assignee: SmithKline & French Laboratories Limited, Welwyne Garden City, England

[21] Appl. No.: 934,492

[22] PCT Filed: Apr. 15, 1991

[86] PCT No.: PCT/GB91/00587

§ 371 Date: Oct. 14, 1992

§ 102(e) Date: Oct. 14, 1992

[87] PCT Pub. No.: WO91/16306

PCT Pub. Date: Oct. 31, 1991

[30] Foreign Application Priority Data

Apr. 17, 1990 [GB] United Kingdom ............... 9008605

[51] Int. Cl.$^5$ ........................................... C07D 209/34
[52] U.S. Cl. ................................. 548/486; 560/18; 560/254
[58] Field of Search ............................................ 548/486

[56] References Cited

U.S. PATENT DOCUMENTS

| | | | |
|---|---|---|---|
| 3,574,232 | 4/1971 | Canas-Rodruigez | 548/486 |
| 4,588,790 | 5/1986 | Gallagher | 548/486 |
| 4,593,033 | 6/1986 | Hartmann | 546/111 |
| 4,629,733 | 12/1986 | Müller et al. | 548/486 |
| 5,010,079 | 4/1991 | Manoury | 548/486 |

FOREIGN PATENT DOCUMENTS

| | | | |
|---|---|---|---|
| 300614 | 1/1989 | European Pat. Off. | 548/486 |
| 91-16306 | 10/1991 | PCT Int'l Appl. | 548/486 |

OTHER PUBLICATIONS

Sagami, Chem. Abstr. vol. 90 Entry 103933u (1978).

*Primary Examiner*—Donald G. Daus
*Attorney, Agent, or Firm*—Mary E. McCarthy; Stephen Venetianer; Edward T. Lentz

[57] ABSTRACT

There is disclosed a process for the preparation of a compound of structure (I)

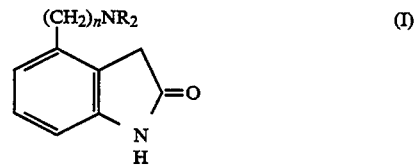

in which n is 1 to 3 and each group R is hydrogen or $C_{1-4}$ alkyl, which comprises, reaction of compound of structure (II)

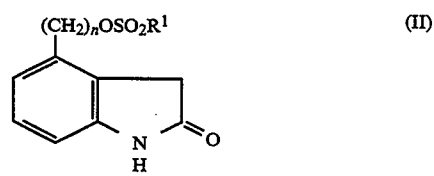

(prepared by esterifying the hydroxyl compound) in which $R^1$ is $C_{1-4}$ alkyl, phenyl or substituted phenyl and n is 1 to 3, with an amine $HNR_2$ in which R is as described for structure (I), and optionally thereafter forming a salt. Intermediates are also disclosed.

8 Claims, No Drawings

PROCESS

The present invention relates to an improved process for the preparation of substituted indolone derivatives. Such compounds are in particular described in EP-0113964-B as being useful in cardiovascular therapy, and in EP-299602-A as agents useful in the treatment of Parkinson's disease.

Processes for the preparation of substituted indolone derivatives have been described in the art, for example in EP-113964-B, and in EP-300614-A1. In particular, EP-300614-A1 describes a series of steps which allow preparation of compounds of the structure

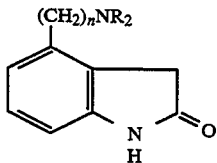

in which R is, inter alia, hydrogen or $C_{1-4}$alkyl and n is 1 to 3, the final step of which comprises displacement by an amine of a halogen leaving group, from the precursor compounds of structure

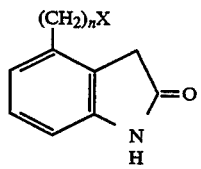

in which X is halogen.

The present invention provides an improvement to the reaction sequence disclosed in EP-300614-A1 and provides, in a first aspect, a process for the preparation of a compound of structure (I)

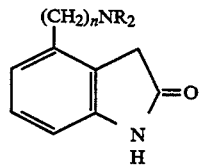

in which n is 1 to 3 and each group R is hydrogen or $C_{1-4}$alkyl, which comprises, reaction of a compound of structure (II)

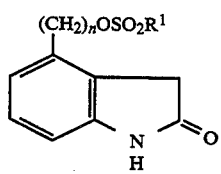

in which n is 1 to 3 and $R^1$ is $C_{1-4}$alkyl, phenyl or substituted phenyl with an amine of structure $HNR_2$ where R is as described for structure (I), and optionally thereafter forming a salt.

Suitably, one of the groups R is hydrogen and the other is hydrogen or $C_{1-4}$alkyl; preferably, both groups R are $C_{1-4}$alkyl, in particular propyl. Suitably n is 1 to 3; preferably n is 2.

Suitably $R^1$ is $C_{1-4}$alkyl such as methyl, phenyl or substituted phenyl, for example p-methylphenyl; preferably $R^1$ is p-methylphenyl.

Suitably, the reaction is carried out in a variety of solvents at elevated temperature, preferably in water, at a temperature of between about 80° and about 90° C.

The compounds of structure (II) are novel and themselves form a further aspect of the invention.

Surprisingly, it has been found that the reaction described herein provides the desired product in much higher yields than previously obtained using the prior art process described in EP-300614-A in which a halogen leaving group is displaced by an amine.

More particularly, it has been found that, for example when used to prepare the compound 4-[2-(di-n-propylamino)ethyl]-1,3-dihydro-2H-indol-2-one hydrochloride salt ((I), n=2, R=n-propyl), from the corresponding precursor (II) in which the leaving group is bromine (rather than $OSO_2R^1$), isolated yields of about 60% are obtained, whereas yields of up to 87% have been obtained from compounds of structure (II) in which an oxygen leaving group is present.

This significant increase in yield could not have been predicted from the prior art disclosure of EP-300614-A or from general prior art knowledge.

As referred to above, the method is particularly useful for the preparation of the compound 4-[2-(di-n-propylamino)ethyl]-1,3-dihydro-2H-indol-2-one hydrochloride salt (INN:ropinirole), a compound useful for the treatment of Parkinson's disease (EP-299-602-A). In addition, when used to prepare the compounds of the invention (and in particular ropinirole) the processes used to prepare the compounds (II), proceed via important intermediates which themselves form a further aspect of the invention. In particular, the compounds (II) can be prepared via the following route:

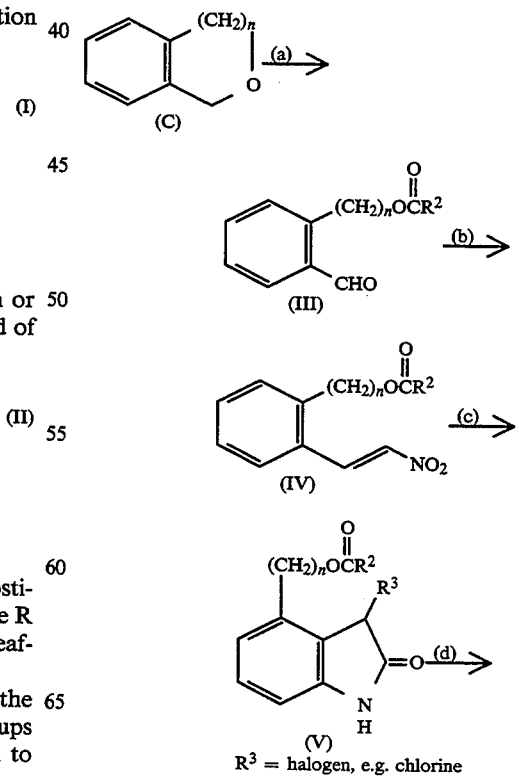

-continued

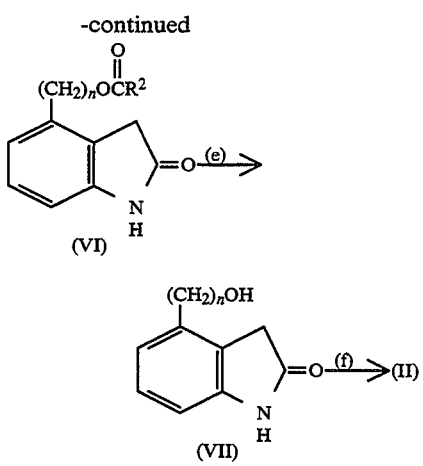

(a) R²COCl, ZnCl₂, CH₂Cl₂ −10°-0°; C₆H₁₂N₄, IMS, Δ; 50% aq. AcOH, Δ; Na₂S₂O₅, IMS, H₂O, CH₂Cl₂, NaHCO₃, 5°-12° C.;
(b) NaOMe, MeNO₂, MeOH, 0°; MeOH/H₂O, HCl;
(c) FeCl₃, AcCl, CH₂Cl₂;
(d) NaH₂PO₂, 10% Pd/C, EtOAc/H₂O;
(e) NaOH, MeOH/H₂O, Δ;
(f) R¹SO₂Cl/Pyridine.

In the above-noted scheme, R¹ and n are as described for formula (II) and R² can be for example, C₁₋₄alkyl, in particular methyl, phenyl or substituted phenyl. Starting compounds (C), are known or can be prepared by standard methods. For example, when used to prepare the preferred compounds of structure (II) in which n is 2, the starting material (C) in which n is 2, i.e. isochroman, is commercially available.

In a further aspect of the invention there is therefore provided compounds of structure (III), (IV), (V), (VI) and (VII) as defined in the scheme above.

Compounds of structure (V) and (VI) can be represented by the following combined structure (VIA):

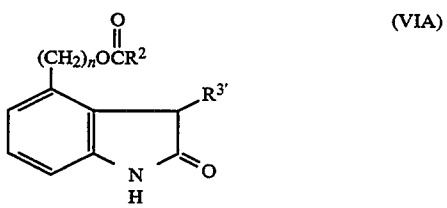

in which n is 1 to 3, R² is C₁₋₄alkyl, phenyl or substituted phenyl, and R³' is hydrogen or halogen.

Compounds of structure (III) and (IV) can be represented by the following combined structure (IVA):

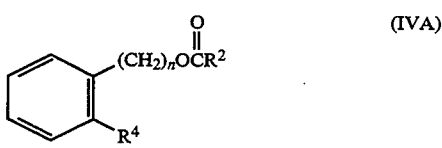

in which n and R² are as described for structure (VIA) and R⁴ is CHO or CH=CHNO₂.

The following examples serve to illustrate the invention. Temperatures are recorded in degrees centigrade.

EXAMPLE 1

Preparation of 4-[2-(di-n-propylamino)ethyl]-1,3-dihydro-2H-indol-2-one hydrochloride A. Preparation of 2-formyl phenethyl benzoate.

To a stirred suspension of ZnCl₂ (61 g 12 equiv.) in CH₂Cl₂ (250 ml) at 5° was added a solution of PhCOCl (63 g, 1.2 equiv.) in CH₂Cl₂ (50 ml) followed by isochroman (50 g, 1 equiv.). [Max temperature during 5° for one hour, by which time, all the isochroman had been consumed.

The reaction mixture was poured onto ice (300 g) and the organic layer was removed and washed with water (2 × 300 ml).

The organic layer was then added to hexamethylenetetramine (105 g, 2 equiv.) in 94% IMS (375 ml), and the reaction mixture was heated in order to remove CH₂Cl₂ via distillation (ca. 90 minutes). 50% Aqueous acetic acid (375 ml) was then added, and the reaction was further heated in order to remove the IMS present via distillation. The reaction mixture was then cooled, and extracted with CH₂Cl₂ (375 ml). The organic layer was washed with water (300 ml), 7% aqueous sodium bicarbonate solution (300 ml) and again with water (300 ml).

To the methylene chloride layer containing crude product was added sodium metabisulphite (77 g), IMS (65 ml) and water (110 ml). The reaction mixture was then heated in order to remove CH₂Cl₂ [maximum pot temperature @50°, maximum distillate temperature @45°] and then cooled to −10°, by which time a thick white precipitate was produced. CH₂Cl₂ (375 ml) was then added, and the white solid was collected at the pump, and washed with cold, fresh CH₂Cl₂ (75 ml).

The damp bisulphate addition complex was added, in portions, to a 7% aqueous sodium bicarbonate solution (1000 ml) at 20°-25°. The pure aldehyde was then extracted into CH₂Cl₂ (375 ml), and the organic layer was then washed with water (2 × 300 ml). After drying (MgSO₄) and filtration, the organic solution was concentrated in vacuo to a base temperature of 70° to leave a pale green mobile oil (61 g, 64%).

In respect of this reaction on a 20 kg scale on pilot-plant facilities, a 26.6 kg (70% yield) of 2-formyl phenethyl benzoate was obtained.

B. Preparation of 2-(2'-benzoyloxyethyl)-β-nitrostyrene.

To a stirred solution of 2-formylphenethyl benzoate (10 g, 1 equiv.) in methanol (40 ml) containing a small amount of 30% wt/wt sodium methoxide in methanol solution (0.5 g), at −10°, was added nitromethane (3.6 g, 1.5 equiv.) and sodium methoxide in methanol (30% wt/wt 8.85 g, 1.2 equiv. total) over a temperature range of −10°-0°. The reaction mixture was then stirred at 10° for 50 minutes, before being added over a 10 minute period to a 3O rapidly stirred methanol/conc. hydrochloric acid (60/60 ml) solution over the temperature range −10°-0°. The quenched reaction mixture was stirred at 0° for 10 minutes before being warmed up to 30° and water (60 ml) was slowly added over a 30 minute period. The yellow solid which was formed was collected at the pump and washed with 50% aqueous methanol (50 ml) and dried at 40°-50° overnight. Yields of the title compound in the region of 85-88% were obtained using this method which contains impurities in the 1-4% wt/wt range. Recrystallisation from isopropanol (3 ml solvent/g product, recovery @80%) gave the pure title compound.

C. Preparation of 4-(2'-benzoyloxyethyl)-3-chloro-1,3-dihydro-2H-indol-2-one

To a stirred suspension of ferric chloride (54.6 g, 4 equiv.) in $CH_2Cl_2$ (250 ml) at 5° was added acetyl chloride (13.2 g, 2 equiv.), followed by a solution of the product from (B) (25 g, 1 equiv.) in $CH_2Cl_2$ (125 ml) over the temperature range 5°–10°. The cooling source was then removed and the reaction temperature rose to 27° over a 30 minute period and after a further 30 minutes, a reaction temperature of 23° was obtained.

The reaction mixture was cooled to 5° and water (375 ml) was added at such a rate that the temperature was kept below 15°. After the addition of water was complete, the quenched mixture was heated to 30° and the organic layer was isolated. The organic layer was then washed with water (3 × 300 ml) at a temperature of 30° for each wash. The organic layer was filtered and then concentrated down to a volume of @150 ml, by which time precipitation of the product had started to occur. Light petroleum (60/80) (100 ml) was then added to the hot $CH_2Cl_2$ mixture and the resulting precipitate was cooled to 5° for 30 minutes. The product was collected at the pump and washed with $CH_2Cl_2$/petrol (60/80) (3:2.50 ml) and then dried. This gave the title compound 16.12 g, 61% yield in the form of an off-white solid.

D. Preparation of 4-(2'-benzoyloxyethyl)-1,3-dihydro-2H-indol-2-one

The product from C (46.7 g, 1 equiv.) and 10% Pd/C (60% wt/wt $H_2O$, 0.011 equiv Pd) were stirred in ethyl acetate (600 ml) and heated to reflux. To this mixture was added an aqueous solution of sodium hypophosphite hydrate (40 g, 2.55 equiv.) in water (100 ml) over a period of 20 minutes. The reaction mixture was heated for a further 30 minutes, and the hot mixture was then filtered through celite and diluted with hot water (100 ml). The resulting water layer was removed and the ethyl acetate solution was concentrated to a volume of @250 ml and cooled to 0°. The resulting precipitate was collected at the pump and dried at 60° overnight. This gave the title compound, 36 g, 86% in the form of a white solid.

E. Preparation of 4-(2'-hydroxyethyl)-1,3-dihydro-2H-indol-2-one.

The product from D (10.25 g, 1 equiv.) and solid sodium hydroxide (1.56 g) were stirred in water (50 ml) and methanol (20 ml) and heated to reflux for 2 hours. Methanol was then removed via distillation and the reaction mixture was then cooled. The pH of the reaction mixture was adjusted to 7 and the creamy white precipitate was collected at the pump, washed with water (120 ml) and dried at 80° overnight to give the title compound, 5.56 g, 89%.

F. Preparation of 2-(2'-oxo-2,3-dihydro-4-indolyl)ethyl toluene sulphonate.

To a stirred solution of the product from E (20 g, 1 equiv.) in pyridine (90 ml, 10 equiv.) at 5°–10° was added a solution of p-toluene sulphonyl chloride (30.2 g, 1.4 equiv.) in $CH_2Cl_2$ (90 ml) at such a rate as to keep the reaction temperature below 10°. The mixture was then stirred at 5°–10° for 2 hours before being added to a stirred solution comprising of concentrated hydrochloric acid (110 ml), water (100 ml) and $CH_2Cl_2$ (90 ml) at a temperature below 15°. The organic layer was removed, and the aqueous phase was extracted with $CH_2Cl_2$ (50 ml). The combined organic extracts were washed with water (2 × 100 ml) and then filtered. $CH_2Cl_2$ (150 ml) was removed via distillation and the residual solution was diluted with 94% IMS (100 ml). Distillation was continued in order to completely remove $CH_2Cl_2$. Water (50 ml) was then added, and the solution was then cooled to 0°. The product was collected at the pump and washed with cold 33% aqueous IMS (60 ml) to give the title compound, 34 g, 91% yield as an off-white solid.

G. Preparation of 4-[2-(di-n-propylamino)ethyl]-1,3-dihydro-2H-indol-2-one hydrochloride Water (420 ml) and di-n-propylamine (124 ml) were mixed and thoroughly purged with $N_2$ at 40° C. for 10 minutes. The product from F (30 g) was then added and the mixture was heated to 80°–5°, under an $N_2$ atmosphere for 2 hours. After this time, the two-phase mixture was allowed to separate and the water layer was removed and replaced with fresh water (210 ml) which had been purged with nitrogen for 10 minutes at ambient temperature. Excess di-n-propylamine was removed via vacuum azeotropic distillation, before the mixture was cooled, and acidified using conc. hydrochloric acid (22 ml). The acidic aqueous phase was extracted twice with $CH_2Cl_2$ (100 ml and 50 ml) and these extracts were discarded.

The aqueous phase was then basified to pH 12–14 using 50% aqueous sodium hydroxide solution, before being extracted with $CH_2Cl_2$ (100 ml and 50 ml). The organic layer was washed twice with water (2 × 100 ml) and then diluted with isopropanol (240 ml), and acidified using conc. hydrochloric acid (17.5 ml). $CH_2Cl_2$ was then removed via atmospheric distillation to a maximum vapour temperature of 75° C. On cooling, an off-white precipitate was formed and this was cooled to 0° before the solid was collected at the pump, and washed with cold isopropanol. After drying, the title compound (23.3 g) was isolated in a 87% yield as an off-white solid.

EXAMPLE 2

Preparation of 4-[2-(di-n-propylamino)ethyl]1,3-dihydro-2H-indol-2-one hydrochloride from 2-(2'-oxo-2,3-dihydro-4-indolyl)ethyl methanesulphonate (A) preparation Of 2- (2'-oxo-2,3-dihydro-4-indolyl)ethyl methanesulphonate To a suspension of the product from 1(E) (10 g, 1 equiv.) in pyridine (60 ml) at 0° C., was added, in small portions, methanesulphonyl chloride (7.1 g, 1.1 equiv.) making sure the temperature did not rise above 5° C. The mixture was then stirred at 0° C. for one hour. T.l.c. analysis showed that the reaction had gone to completion.

The reaction mixture was quenched into 2.4M hydrochloric acid (250 ml) at 0°–10° C., and was then extracted with ethyl acetate (2 × 200 ml). The combined extracts were then washed with water (2 × 100 ml), dried, filtered, and concentrated in vacuo to give the title compound as a white solid. This was recrystallised from 94% IMS to give an isolated yield of 9.5 g, 66%.

(B) Preparation of 4-[2-(di-n-propylamino]ethyl]-1,3-dihydro-2H-indol-2-one hydrochloride The methanesulphonate derivative from (A) (8.3 g, 1 equiv.) was stirred with di-n-propylamine (32.4 g, 10 equiv.) and water (120 ml) at 80° C. for two hours. HPLC analysis showed that the reaction had gone to completion.

Excess di-n-propylamine was removed by vacuum azeotropic distillation. The mixture was then cooled, and basified to pH 14 using solid sodium hydroxide. The basic aqueous mixture was then extracted with dichloromethane (3 × 50 ml), and the combined extracts were washed with water (2 × 100 ml). After drying and filtration, the organic solution was concentrated totally in vacuo to leave a purple oil.

The oil was dissolved in isopropanol (200 ml) and cooled to 0° C., before conc. hydrochloric acid was added. The resulting precipitate was collected by filtration, washed with cold isopropanol (10 ml) and dried to give the title compound, 7.1 g, 75%.

EXAMPLE 3

Preparation of 4-[2-(di-n-propylamino)ethyl]-1,3-dihydro-2H-indol-2-one hydrochloride from 2-(2'-oxo-2,3-dihydro-4-indolyl)ethyl benzenesulphonate (A) Preparation of 2-(2'-oxo-2,3-dihydro-4-indolyl)ethyl benzenesulphonate To a suspension of the product from 1(E) (5 g, 1 equiv.) in pyridine (30 ml) at −30° C., was added benzenesulphonyl chloride (5.5 g, 1.1 equiv.), ensuring the temperature remained below −20° C. The mixture was then stirred at −30° C. for 5 hours.

The reaction mixture was quenched into 2.4M hydrochloric acid (125 ml) at −10° to −5° C., and the acidic aqueous phase was then extracted into ethyl acetate (200 and 100 ml). The combined organic extracts were washed with water (150 ml), dried, filtered and then concentrated in vacuo to give a beige solid. This was recrystallised from IMS giving the title compound, 6.1 g, 69%.

(B) preparation of 4-[2-(di-n-propylamino)ethyl]-1,3-dihydro-2H-indol-2-one hydrochloride The benzenesulphonyl derivative from (A) (5 g, 1 equiv.) was stirred with di-n-propylamine (16 g, 10 equiv.) and water (100 ml) at 80° C. for 2½ hours. Excess di-n-propylamine was removed via vacuum azeotropic distillation. The remaining aqueous phase was then basified to pH 14 using solid sodium hydroxide, and then extracted using dichloromethane (2 × 50 ml). The combined extracts were washed with water (2 × 100 ml), dried, and concentrated in vacuo to leave a purple oil.

The oil was dissolved in isopropanol (100 ml) and the solution cooled to 0° C., before conc. hydrochloric acid was added (5 ml). Isopropanol (40 ml) was then removed via atmospheric distillation, before the mixture was cooled to 0° C. to give a fine precipitate.

The desired product was collected via filtration, washed with cold ispropanol (10 ml), and dried to give the desired product (3.3 g, 70%).

We claim:

1. A process for the preparation of a compound of structure (I)

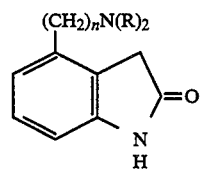

in which n is 1 to 3 and each group R is hydrogen or $C_{1-4}$alkyl, which comprises, reaction of a compound of structure (II)

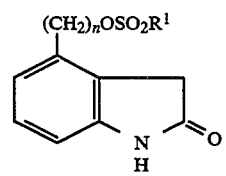

in which $R^1$ is $C_{1-4}$alkyl, phenyl or phenyl substituted by $C_{1-4}$ alkyl and n is 1 to 3, with an amine $NH(R)_2$ in which R is as described for structure (I), and optionally thereafter forming a salt.

2. A process according to claim 1 in which $R^1$ is p-methylphenyl.

3. A process according to claim 2 in which both groups R are $C_{1-4}$alkyl and n is 2.

4. A process according to claim 1 in which the compound of structure (I) prepared is:
   4-[2-(di-n-propylamino)ethyl]-1,3-dihydro-2H-indol-2-one hydrochloride (INN: ropinirole).

5. A process according to claim 2 in which the compound of structure (I) prepared is:
   4-[2-(di-n-propylamino)ethyl]-1,3-dihydro-2H-indol-2-one hydrochloride (INN: ropinirole).

6. A compound of structure (II):

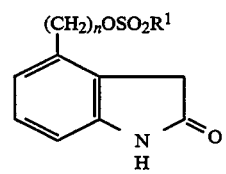

in which n is 1 to 3 and $R^1$ is $C_{1-4}$alkyl, phenyl or phenyl substituted by $C_{1-4}$ alkyl.

7. A compound of structure (VII):

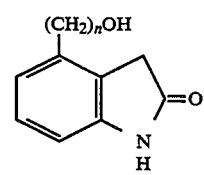

in which n is 1 to 3.

8. A compound of structure (VIA):

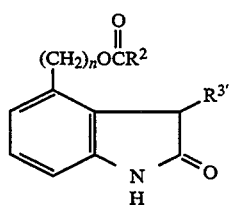

in which n is 1 to 3, $R^2$ is $C_{1-4}$ alkyl, phenyl or phenyl substituted by $C_{1-4}$ alkyl and $R^{3'}$ is hydrogen or halogen.

* * * * *